US010124653B2

(12) United States Patent
Esses

(10) Patent No.: US 10,124,653 B2
(45) Date of Patent: Nov. 13, 2018

(54) MOBILE DEVICE HOLDER AND AIR FRESHENER

(71) Applicant: Alfred Esses, Brooklyn, NY (US)

(72) Inventor: Alfred Esses, Brooklyn, NY (US)

(73) Assignee: Alfred Esses, Brooklyn, NY (US)

( * ) Notice: Subject to any disclaimer, the term of this patent is extended or adjusted under 35 U.S.C. 154(b) by 261 days.

(21) Appl. No.: 14/463,176

(22) Filed: Aug. 19, 2014

(65) Prior Publication Data
US 2016/0052370 A1 Feb. 25, 2016

(51) Int. Cl.
*A61L 9/12* (2006.01)
*B60H 3/00* (2006.01)
*B60R 11/02* (2006.01)

(52) U.S. Cl.
CPC .............. *B60H 3/0028* (2013.01); *A61L 9/12* (2013.01); *B60R 11/02* (2013.01)

(58) Field of Classification Search
CPC . A61L 9/12; A61L 9/122; A61L 9/127; B60R 11/00; B60R 11/02; B60H 3/0028
USPC ........... 239/34, 53–58, 60, 6; 454/156, 157; 362/92
See application file for complete search history.

(56) References Cited

U.S. PATENT DOCUMENTS

| | | | |
|---|---|---|---|
| 5,932,147 A * | 8/1999 | Chen ....................... | A61L 9/122 239/56 |
| 6,099,137 A | 8/2000 | McCormack | |
| 6,102,660 A | 8/2000 | Lee | |
| 6,398,381 B1 * | 6/2002 | Tseng ....................... | A61L 9/12 362/234 |
| 6,932,331 B1 | 8/2005 | Fan | |
| 7,687,037 B2 | 3/2010 | Wheatley et al. | |
| 7,687,038 B2 | 3/2010 | Wheatley et al. | |
| 8,480,960 B2 | 7/2013 | Wheatley et al. | |
| 8,662,480 B1 | 3/2014 | Irvin | |
| 8,673,223 B1 | 3/2014 | Finlay | |
| 2010/0061896 A1 * | 3/2010 | Sassoon ............... | A01M 1/2033 422/124 |
| 2011/0116977 A1 * | 5/2011 | Yamamoto .......... | A01M 1/2033 422/124 |

(Continued)

FOREIGN PATENT DOCUMENTS

CN 200947724 Y 9/2007
CN 202641316 U 1/2013

(Continued)

*Primary Examiner* — Alexander Valvis
*Assistant Examiner* — Tuongminh Pham
(74) *Attorney, Agent, or Firm* — Moritt Hock & Hamroff LLP; Bret P. Shapiro

(57) ABSTRACT

Technologies are generally described for systems, devices and methods relating to a mobile device holder and air freshener. The mobile device holder and air freshener may include a body, a top portion, a bottom portion, and a removable cap. The body may be arranged so as to include a first interior that is at least partially hollow. The top portion and the bottom portion may be effective to hold a mobile electronic device. The removable cap may include a first vent effective to allow air to flow into the device. The removable cap may allow scented material to be installed within the mobile device holder and air freshener. The body may be further arranged so as to allow air that has entered the device through the first vent to become scented and flow out of the device through a second vent included in the device.

13 Claims, 5 Drawing Sheets

(56) References Cited

U.S. PATENT DOCUMENTS

| | | | |
|---|---|---|---|
| 2013/0164178 A1 | 6/2013 | Carmichael | |
| 2013/0266486 A1 | 10/2013 | Wu | |
| 2014/0112649 A1 | 4/2014 | Irvin et al. | |
| 2014/0124594 A1 | 5/2014 | Hsiao | |
| 2014/0158789 A1 | 6/2014 | Haymond | |
| 2014/0161672 A1 | 6/2014 | Wheatley et al. | |
| 2015/0355693 A1* | 12/2015 | Chang .................... | G06F 1/203 |
| | | | 361/679.48 |

FOREIGN PATENT DOCUMENTS

| | | |
|---|---|---|
| CN | 202950996 U | 5/2013 |
| DE | 202004002799 U | 6/2004 |
| GB | 2062199 A | 5/1981 |
| GB | 2292271 A | 2/1996 |
| KR | 2012015933 A | 11/2012 |
| KR | 20120125933 A | 11/2012 |

\* cited by examiner

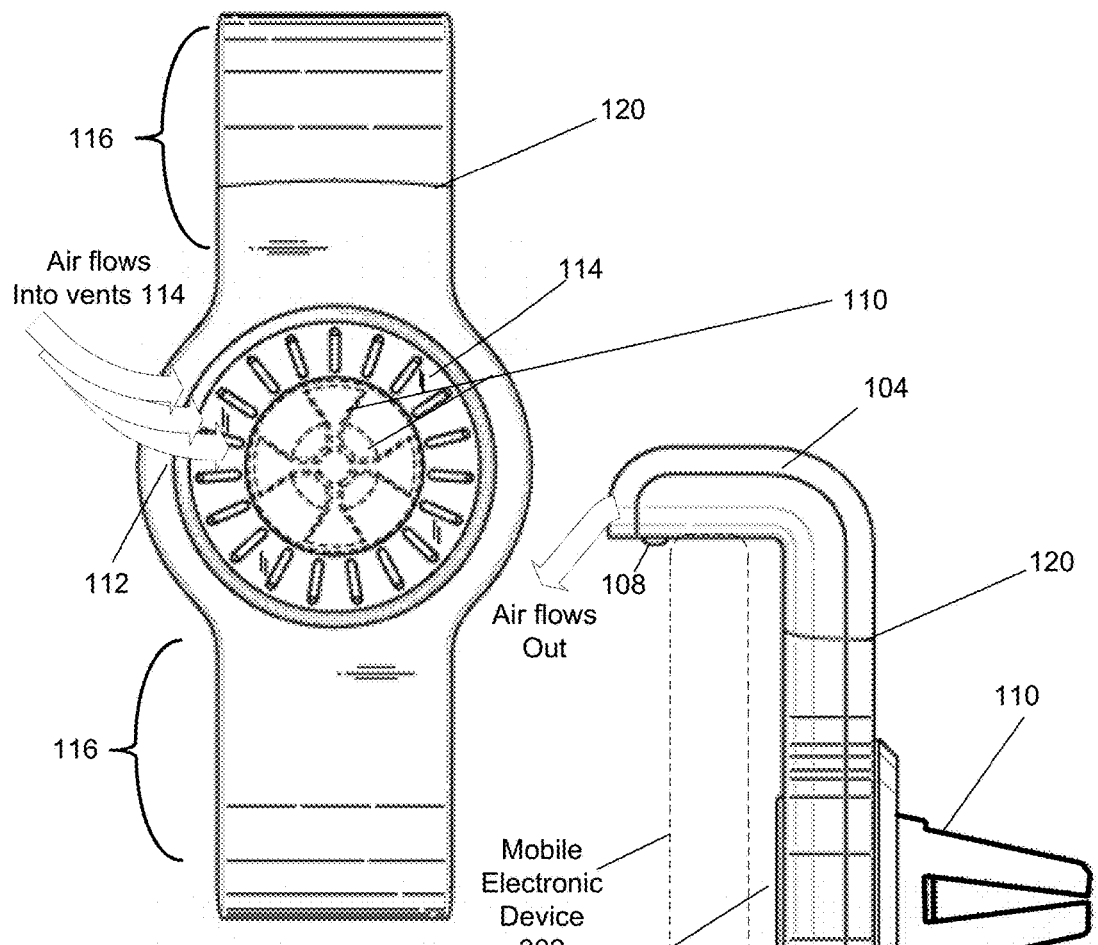
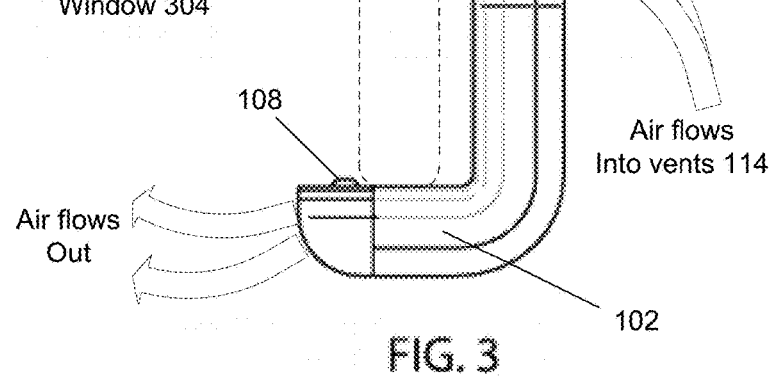

US 10,124,653 B2

MOBILE DEVICE HOLDER AND AIR FRESHENER

BACKGROUND

Air fresheners reduce or mask undesired odors and emit pleasant odors. Air fresheners typically emit a pleasant odor in the form of a fragrance. Air fresheners include sprays, candles, oils, gels, and plug-ins.

SUMMARY OF THE INVENTION

In an example, devices are generally described. In some examples, the devices may include a body. The body may be arranged so as to include a first interior that is at least partially hollow. In some other examples, the devices may include a top portion and a bottom portion. In various examples, the top portion and the bottom portion may be effective to hold a mobile electronic device between the top portion and the bottom portion. In some further examples, the devices may further include a removable cap. The removable cap may include a first vent effective to allow air to flow into the device. In some examples, the removable cap may be removable to allow scented material to be installed within the first interior or within a second interior of the removable cap. In various examples, the body may be further arranged so as to allow air that has entered the device through the first vent to become scented and flow out of the device through a second vent included in the device.

In another example, methods to secure a mobile electronic device in an air freshener device are generally described. In some examples, the methods may include placing the mobile electronic device between a top portion and a bottom portion of the air freshener device so that a rear portion of the mobile electronic device is arranged along a surface of a body of the air freshener device. In various examples, the body may be arranged to include a first interior that is at least partially hollow. In some examples, the body may include a first arm attached to the top portion and a second arm attached to the bottom portion. In some further examples, the methods may further include arranging a removable cap in connection with the body. The removable cap may include a first vent effective to allow air to flow into the device. In some examples, the removable cap may be removable to allow scented material to be installed within the first interior or a second interior of the removable cap. In some further examples, the methods may include adjusting a length of at least one of the first arm and the second arm to secure the mobile electronic device between the top portion and the bottom portion. In other examples, the body may be sized and shaped so as to allow air that has entered the air freshener device through the first vent to become scented and flow out of the air freshener device through a second vent included in the air freshener device.

In another example, methods to release fragrance from a scented material are generally described. In various examples, the methods may include placing the material inside an interior of a body of an air freshener device. In some examples, the air freshener device may be arranged in such a way as to hold a mobile electronic device. In some further examples, the methods may further include clipping the air freshener device onto an automobile vent. In various other examples, the methods may further include blowing air through the automobile vent so that the air passes through a first vent in the air freshener device. In some examples, particulate matter from the scented material may be effective to mix with the air to create scented air. In some examples, the methods may further include blowing the scented air out of a second vent of the air freshener device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

FIG. 2 is a rear view of a mobile device holder and air freshener;

FIG. 3 is a side view of a mobile device holder and air freshener;

Figure 1:
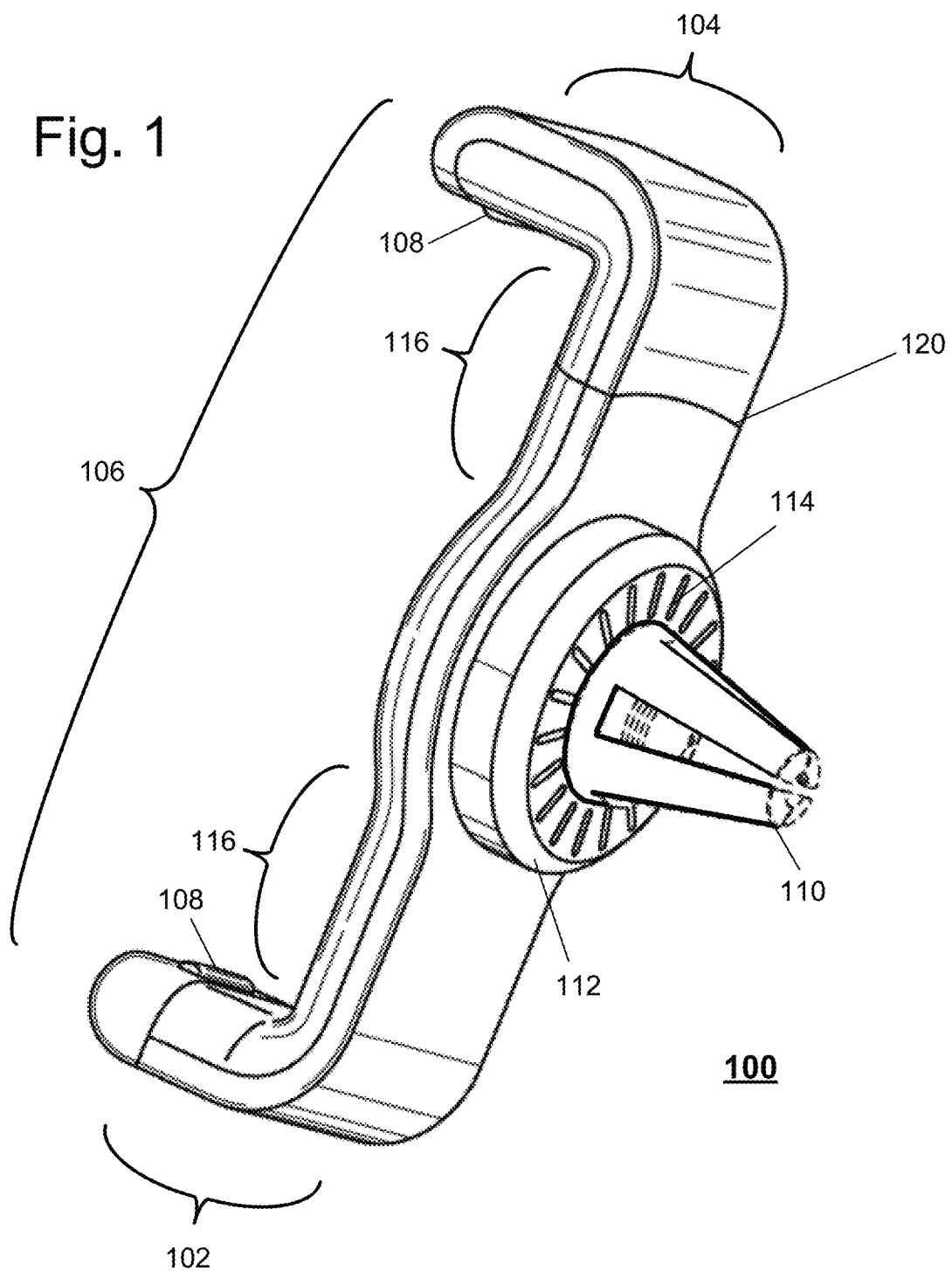
FIG. 1 is an angled side perspective of a mobile device holder and air freshener.

all in accordance with an embodiment of the invention.

DETAILED DESCRIPTION

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

FIG. 1 is an angled side perspective of a mobile device holder and air freshener in accordance with an embodiment of the invention. A mobile device holder and air freshener 100 may include a body 106, a bottom portion 102, a top portion 104, a removable cap 112, and/or a clip 110. Body 106 may include arms 116. Arms 116 may attach top portion 104 and bottom portion 102 to body 106 of mobile device holder and air freshener 100. In some examples, body 106, top portion 104, and/or bottom portion 102 may be arranged so as to include an interior that is at least partially hollow, such that air may flow through cavities within body 106, top portion 104, and/or bottom portion 102 of mobile device holder and air freshener 100. In some examples, top portion 104 and bottom portion 102 may be arranged at an angle that is perpendicular to or substantially perpendicular to arms 116. Top portion 104 and bottom portion 102 may include flanges 108. Flanges 108 may include raised material relative to an otherwise uniform, planar surface top portion 104 and/or bottom portion 102 of mobile device holder and air freshener 100. Flanges 108 may be configured to prevent a mobile electronic device installed or held between top portion 104 and bottom portion 102 of mobile device holder and air freshener 100 from falling out of mobile device holder and air freshener 100. In some other examples, a length of arms 116 may be adjustable. For example, a length of arms 116 may be adjusted axially such that top portion 104 and bottom portion 102 may be moved closer together and/or further apart from one another. In some examples, to be discussed in further detail below, arms 116 may be axially adjusted to hold and/or secure a mobile electronic device placed between top portion 104 and bottom portion 102. In some examples, flanges 108 may be effective to prevent a mobile electronic device installed in mobile device holder and air freshener 100 from becoming uninstalled or dislodged from between top portion 104 and bottom portion 102 of mobile device holder and air freshener 100. In some further examples, arms 116 may separate at one or more seams, such as seam 120, so that arms 116 may be adjusted. In some examples, seam 120 may be a line of division between an upper portion of arm 116 and a lower portion of arm 116.

Removable cap 112 may be removed from a coupling or connection to body 106 in order to install or replace scented material within body 106 and/or within an interior of removable cap 112 of mobile device holder and air freshener 100. In some examples, scented material may be a liquid oil, gel, aerosol, or solid material (such as ceramic, paper, etc.) infused with a fragrance. In some other examples, scented material may include scented oil encapsulated by a plastic ring or disc. The plastic ring or disc may include a membranous portion effective to allow scented oil to escape the ring or disc. The scented oil may evaporate, allowing scented particles to mix with the air to create scented air. In some examples, heating the oil may accelerate the evaporation of the oil. In some other examples, air flowing over the oil may accelerate evaporation of the oil. Fragrances may be any desirable fragrance, including fruit scents, new car smell, etc. Removable cap 112 may be arranged in such a way that removable cap 112 includes vents 114. Vents 114 may allow air to flow into and out of an interior of body 106. In some examples, air blown into and/or out of mobile device holder and air freshener 100 may be scented by scented material within body 106 and/or cap 112.

Removable cap 112 may include clip 110. Clip 110 may be effective to clip onto various objects in order to secure mobile device holder and air freshener 100 to the objects. In an example, clip 100 may clip onto the vents of an automobile climate system or onto the blade-guards surrounding a home or office fan. Although depicted as being affixed to removable cap 112, clip 110 may be affixed to arms 116 and/or removable cap 112. In some further examples, clip 110 may be configured to rotate such that a mobile electronic device held by mobile device holder and air freshener 100 may be displayed horizontally, vertically, or at other angles relative to the ground. Air blowing from the automobile climate system or fan may flow into or enter body 106 of mobile device holder and air freshener 100 through vents 114. Air blowing into body 106 of mobile device holder and air freshener 100 may become scented by interaction with scented material within body 106 and/or cap 112. In some examples, particulate matter from the scented material may mix with air blowing into body 106 and/or removable cap 112. Air flowing out of mobile device holder and air freshener 100 may be scented air, as particulate from a scented material within body 106 and/or removable cap 112 may have mixed with the air.

FIG. 2 depicts a rear view of mobile device holder and air freshener 100. Arms 116 may be extended from body 106 and/or shortened into body 106 such that mobile electronic devices of different dimensions may be securely installed in mobile device holder and air freshener 100. FIG. 3 depicts a side view of an air freshener. As depicted, an installed mobile electronic device 302 may be installed in mobile device holder and air freshener 100 between top portion 104 and bottom portion 102. In some examples, mobile electronic device 302 may be an electronic device such as a mobile phone, a tablet computing device, a global positioning system, an electronic reader or another electronic device. Arms 116 may be axially extended from body 106 and/or shortened into body 106, such that differently sized mobile electronic devices may be installed or secured between top portion 104 and bottom portion 102. For example, one or more of arms 116 may separate along seam 120. Flanges 108 may prevent installed mobile electronic device 302 from dislodging from mobile device holder and air freshener 100. Additionally, a rear portion of mobile electronic device 302 may be arranged along body 106 and/or a window 304 when mobile electronic device 302 is installed in mobile device holder and air freshener 100. In some examples, air flowing through vents 114 may flow through body 106 of mobile device holder and air freshener 100 and out of vents which may be included in top portion 104 and/or bottom portion 102 of mobile device holder and air freshener 100.

In some examples, window 304 may be arranged on a front portion of mobile device holder and air freshener 100. Window 304 may be formed from a transparent material such as plastic or glass. In some examples, window 304 may allow a user of mobile device holder and air freshener 100 to see an amount of scented material remaining inside an interior of mobile device holder and air freshener 100. In other examples, heat produced by mobile electronic device 302 may accelerate the release of particulate scented matter from scented material installed within removable cap 112 and/or body 106.

Figure 4:
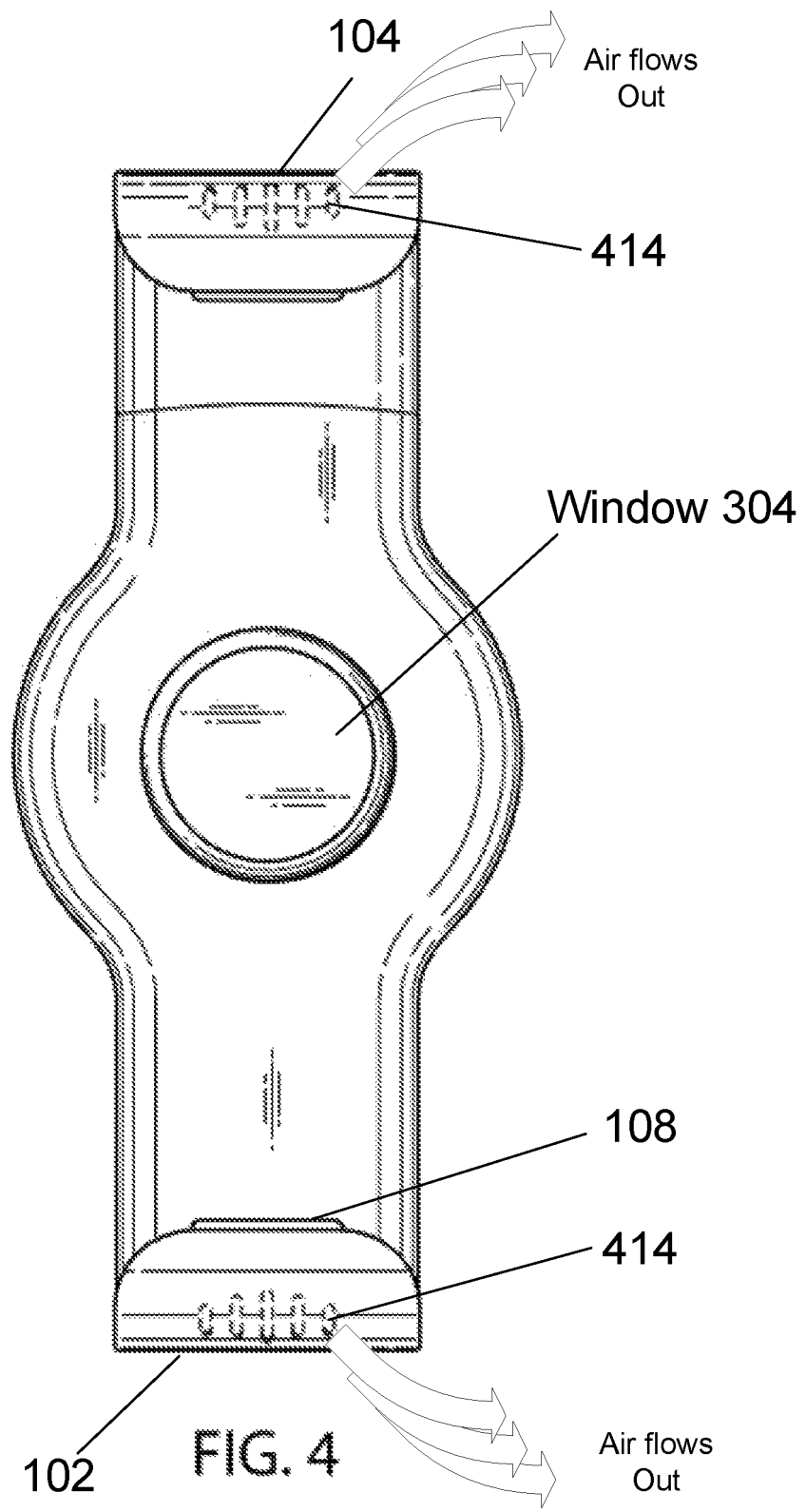
FIG. 4 is a front view of a mobile device holder and air freshener.

FIG. 4 depicts a front view of mobile device holder and air freshener 100. As depicted, mobile device holder and air freshener 100 may include window 304. As depicted, bottom portion 102 may be arranged in such a way as to include vents 414. Vents 414 may allow air blown into mobile device holder and air freshener 100 through vents 114 to escape from body 106 of mobile device holder and air freshener 100. In some examples, air escaping from vents 414 may be scented as a result of mixing with scented particulates released from a scented material installed within mobile device holder and air freshener 100.

Figure 5:
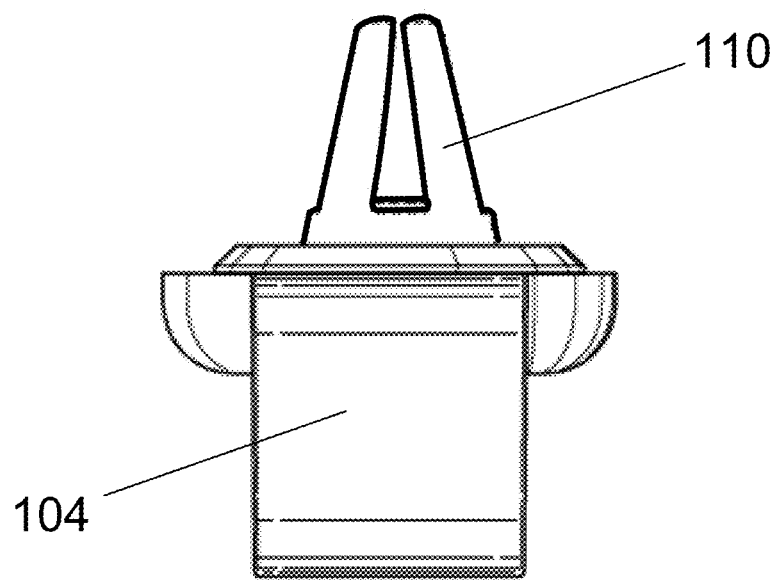
FIG. 5 is a top view of a mobile device holder and air freshener.
Figure 6:
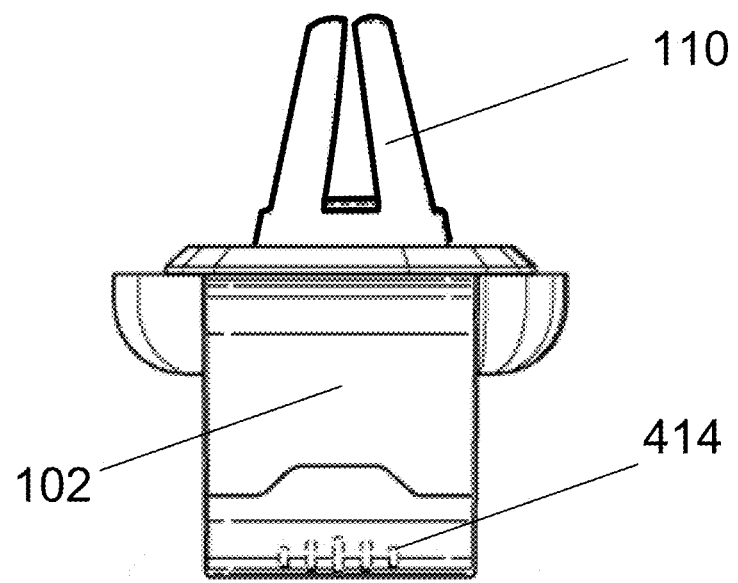
FIG. 6 is a bottom view of a mobile device holder and air freshener.

FIGS. 5 and 6 depict a top view and bottom view, respectively of mobile device holder and air freshener 100. Although vents 414 are depicted as being included in bottom portion 102, vents 414 may be included in top portion 104, bottom portion 102 and top portion 104, or in other locations along mobile device holder and air freshener 100. In some examples, other locations may include front portion 402, arms 116, and/or body 106.

Figure 7:
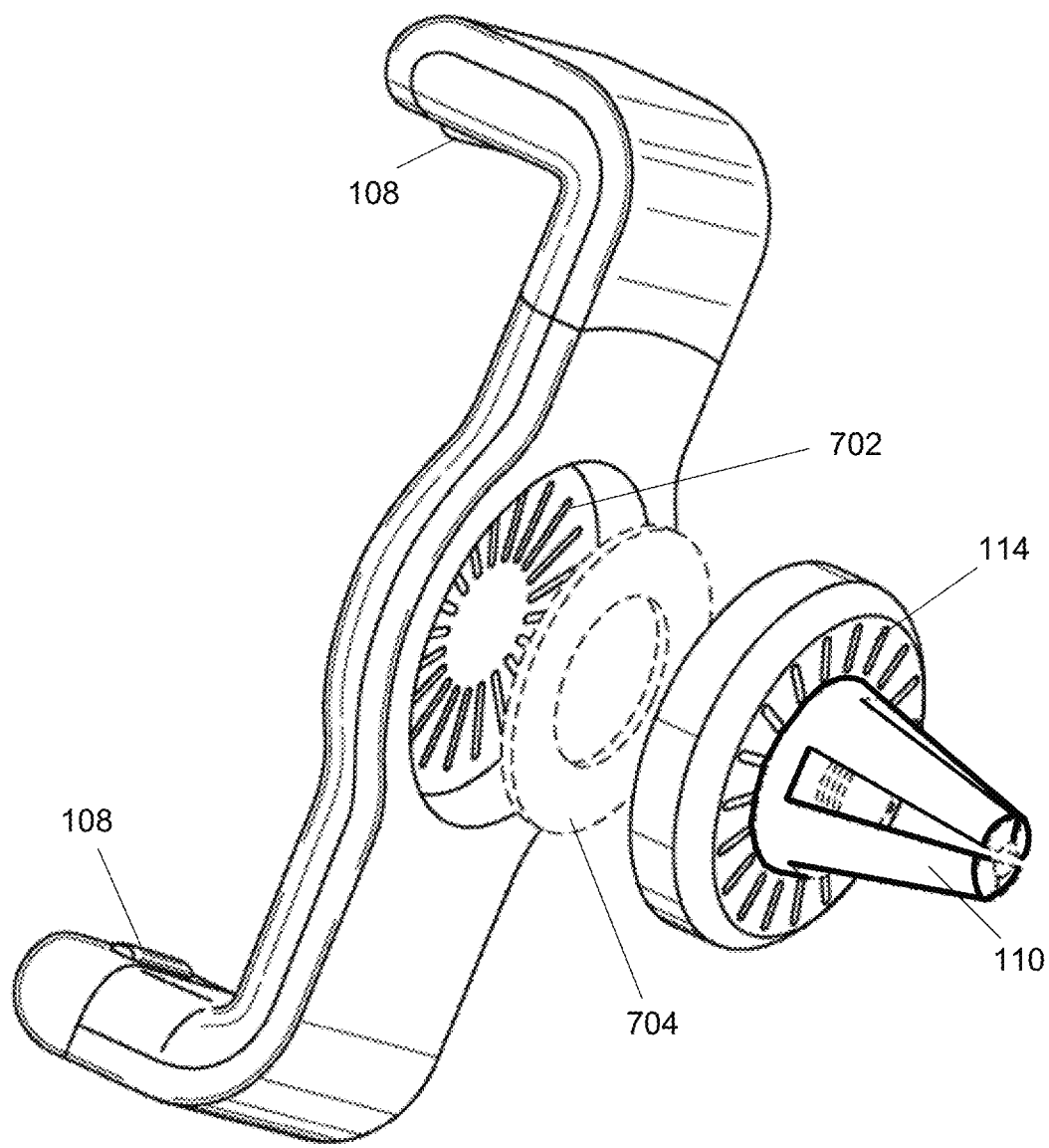
FIG. 7 is an angled side perspective, exploded view illustrating a body, a disk, and a cap enclosure of a mobile device holder and air freshener.

FIG. 7 depicts an angled side perspective, exploded view of mobile device holder and air freshener 100. As discussed, scented material may be installed within mobile device holder and air freshener 100. In an example, the scented material may include a scented material 704. In an example, scented material 704 may be in the shape of a flat ring or disc. In some examples, scented material 704 may be encapsulated by a capsule. In some examples, such a capsule may be ring or disc shaped. A capsule may include a membranous portion effective to allow scented oil to escape from the capsule. In some other examples, scented material 704 may take a different shape which may be optimized for installation and/or production of scented particulate within mobile device holder and air freshener 100. In some examples, body 106 of mobile device holder and air freshener 100 may be arranged in such a way as to include vents 702 in a front portion of mobile device holder and air freshener 100. Vents 702 may allow air and/or heat to flow into and out of mobile device holder and air freshener 100. In some examples, heat from a mobile electronic device installed within mobile device holder and air freshener 100 may flow through vents 702 and may increase an amount of particulate released from scented material 704.

Among other potential benefits, a mobile device holder and air freshener may be secured to a vent in an automobile. A mobile electronic device held by the mobile device holder and air freshener may be easily visible to a driver of an automobile as a result of the mobile device holder and air freshener being conveniently positioned and/or rotated to be within a driver's field of vision. The hollow interior of the mobile device holder and air freshener may allow air to blow from the ventilation system of the automobile through the mobile device holder and air freshener. Air blown through the mobile device holder and air freshener may become scented by scented material within the mobile device holder and air freshener. Thus, mobile device holder and air freshener may allow a driver to view a mobile phone in a convenient position while also providing a pleasant scent within the passenger compartment of the automobile. Additionally, the removable cap of the mobile device holder and air freshener may allow scented material to be easily replaced when older scented material has lost efficacy.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
    a body, wherein the body is arranged so as to include a first interior that is at least partially hollow and the body includes a top arm and a bottom arm;
    a top portion attached to the body at a top end of the top arm and a bottom portion attached to the body at a bottom end of the bottom arm, wherein the top portion and the bottom portion are configured to be adjustable with respect to each other so as to hold a mobile electronic device between the top portion and the bottom portion;
    a removable cap, wherein the removable cap includes a first vent configured to allow air to flow into the device, and wherein the removable cap is removable from the body to allow scented material to be installed within the first interior or within a second interior of the removable cap; and
    wherein the body is further arranged so as to allow air that has entered the device through the first vent to become scented and flow out of the device through a second vent included in the device, and wherein the second vent is included in the top portion of the device.

2. The device of claim 1, wherein the device further includes a clip affixed to the device, wherein the clip is configured to clip the device onto an object.

3. The device of claim 2, wherein the clip is located on the removable cap.

4. The device of claim 1, wherein the top portion and the bottom portion are arranged at perpendicular angles relative to the body.

5. The device of claim 1, wherein the device further includes a third vent, wherein the third vent is included in the bottom portion of the device.

6. The device of claim 1, wherein the top portion and/or the bottom portion includes a flange, wherein the flange is configured to prevent the mobile device from being dislodged from between the top portion and the bottom portion.

7. The device of claim 1, wherein the top and bottom arms are configured to extend from the body to allow the mobile electronic device to be installed between the top portion and the bottom portion.

8. A device comprising:
    a body, wherein the body is arranged so as to include a first interior that is at least partially hollow and the body includes a top arm and a bottom arm;
    a top portion attached to the body at a top end of the top arm and a bottom portion attached to the body at a bottom end of the bottom arm, wherein the top portion and the bottom portion are configured to be adjustable with respect to each other so as to hold a mobile electronic device between the top portion and the bottom portion;
    a removable cap, wherein the removable cap includes a first vent configured to allow air to flow into the device, and wherein the removable cap is removable from the body to allow scented material to be installed within the first interior or within a second interior of the removable cap; and
    wherein the body is further arranged so as to allow air that has entered the device through the first vent to become scented and flow out of the device through a second vent included in the device, wherein the second vent is included in the bottom portion of the device.

9. The device of claim 8, wherein the device further includes a clip affixed to the device, wherein the clip is configured to clip the device onto an object.

10. The device of claim 9, wherein the clip is located on the removable cap.

11. The device of claim 8, wherein the top portion and the bottom portion are arranged at perpendicular angles relative to the body.

12. The device of claim 8, wherein the top portion and/or the bottom portion includes a flange, wherein the flange is configured to prevent the mobile device from being dislodged from between the top portion and the bottom portion.

13. The device of claim 8, wherein the top and bottom arms are configured to extend from the body to allow the mobile electronic device to be installed between the top portion and the bottom portion.

* * * * *